(12) United States Patent
Vajentic

(10) Patent No.: US 7,854,070 B1
(45) Date of Patent: Dec. 21, 2010

(54) FRAMING SQUARE

(76) Inventor: Marko A. Vajentic, 326 Main St., Medfield, MA (US) 02052-2097

( * ) Notice: Subject to any disclaimer, the term of this patent is extended or adjusted under 35 U.S.C. 154(b) by 0 days.

(21) Appl. No.: 12/583,266

(22) Filed: Aug. 18, 2009

(51) Int. Cl.
   *B43L 7/12* (2006.01)
   *B43L 7/14* (2006.01)
(52) U.S. Cl. .............................. 33/417; 33/420; 33/421
(58) Field of Classification Search .................. 33/417, 33/415, 416, 418, 419, 420, 421, 423, 424, 33/425, 426
   See application file for complete search history.

(56) References Cited

U.S. PATENT DOCUMENTS

| | | | | |
|---|---|---|---|---|
| 35,159 | A * | 5/1862 | Iseman | .................... 33/420 |
| 168,656 | A | 10/1875 | McInnes | |
| 189,311 | A | 4/1877 | Klinglesmith | |
| 223,727 | A * | 1/1880 | Halley | ................... 33/419 |
| 243,592 | A | 6/1881 | Marvick | |
| 303,861 | A | 8/1884 | King | |
| 327,283 | A | 9/1885 | Levy | |
| 360,465 | A | 4/1887 | Patterson | |
| 456,216 | A * | 7/1891 | French | .................... 33/420 |
| 516,575 | A | 3/1894 | Parkhill | |
| 538,051 | A | 4/1895 | Taylor | |
| 539,534 | A | 5/1895 | McKinney | |
| 614,144 | A | 11/1898 | Thompson | |
| 614,259 | A | 11/1898 | Bouldry | |
| 666,346 | A * | 1/1901 | Goelzer | ................... 33/420 |
| 738,224 | A | 9/1903 | Morse | |
| 792,212 | A * | 6/1905 | Heddle | ................... 33/421 |
| 828,792 | A | 8/1906 | White | |
| 866,111 | A * | 9/1907 | Cory | ..................... 33/420 |
| 935,067 | A | 9/1909 | Taylor | |
| 940,067 | A | 11/1909 | Richter | |
| 973,584 | A * | 10/1910 | Thomas | .................... 33/341 |
| 1,006,815 | A | 10/1911 | Wiegman | |
| 1,050,969 | A | 1/1913 | McLeod | |
| 1,056,917 | A | 3/1913 | Len | |
| 1,074,969 | A | 10/1913 | Moore | |
| 1,187,272 | A | 6/1916 | Demmrich | |
| 1,189,983 | A | 7/1916 | McLeod | |
| 1,237,790 | A | 8/1917 | Kidder | |
| 1,249,496 | A | 12/1917 | Reveal | |
| 1,301,166 | A * | 4/1919 | Potter | ................... 33/420 |
| 1,337,107 | A | 4/1920 | Van Nest | |
| 1,770,304 | A | 7/1930 | Ferris | |
| 1,916,638 | A | 7/1933 | Riziano | |
| D142,051 | S | 8/1945 | White | |
| 3,015,163 | A | 1/1962 | Cummings | |
| 3,153,859 | A | 10/1964 | Jones | |
| 4,955,141 | A | 9/1990 | Welch | |

(Continued)

*Primary Examiner*—Christopher W Fulton
(74) *Attorney, Agent, or Firm*—John P. McGonagle

(57) ABSTRACT

A square with longitudinal slots in the angular arms, a rule having a longitudinal slot, and two clamping screws for securing the rule in various angular positions on the arms of the square, so that the scale may be shifted on the square to establish a number of angles, and be maintained at its adjusted position. Spirit levels are provided on each of the square arms and on the rule. The square arms and rule are thick thereby providing saw guides. The square arms are each marked with measuring scales as well as with markers for twelve inch or sixteen inch center layouts. The rule is marked with a plurality of degrees for common pitch lines and hip and valley pitch lines.

3 Claims, 8 Drawing Sheets

U.S. PATENT DOCUMENTS

| | | |
|---|---|---|
| 5,170,568 A | 12/1992 | Wright |
| 5,384,967 A | 1/1995 | Helmuth |
| 5,388,340 A | 2/1995 | Marty |
| D364,574 S | 11/1995 | Utz et al. |
| D416,501 S | 11/1999 | DiGangi et al. |
| 6,122,834 A | 9/2000 | Rester |
| D440,889 S | 4/2001 | Frescas |
| D444,718 S | 7/2001 | Ross et al. |
| 6,591,511 B1 | 7/2003 | Carroll et al. |
| 6,868,616 B2 | 3/2005 | Allemand |
| D511,698 S | 11/2005 | Allemand |
| 7,266,899 B2 | 9/2007 | Sanders |
| 7,350,306 B2 | 4/2008 | Reed et al. |
| 2006/0277776 A1 | 12/2006 | Paul |

* cited by examiner

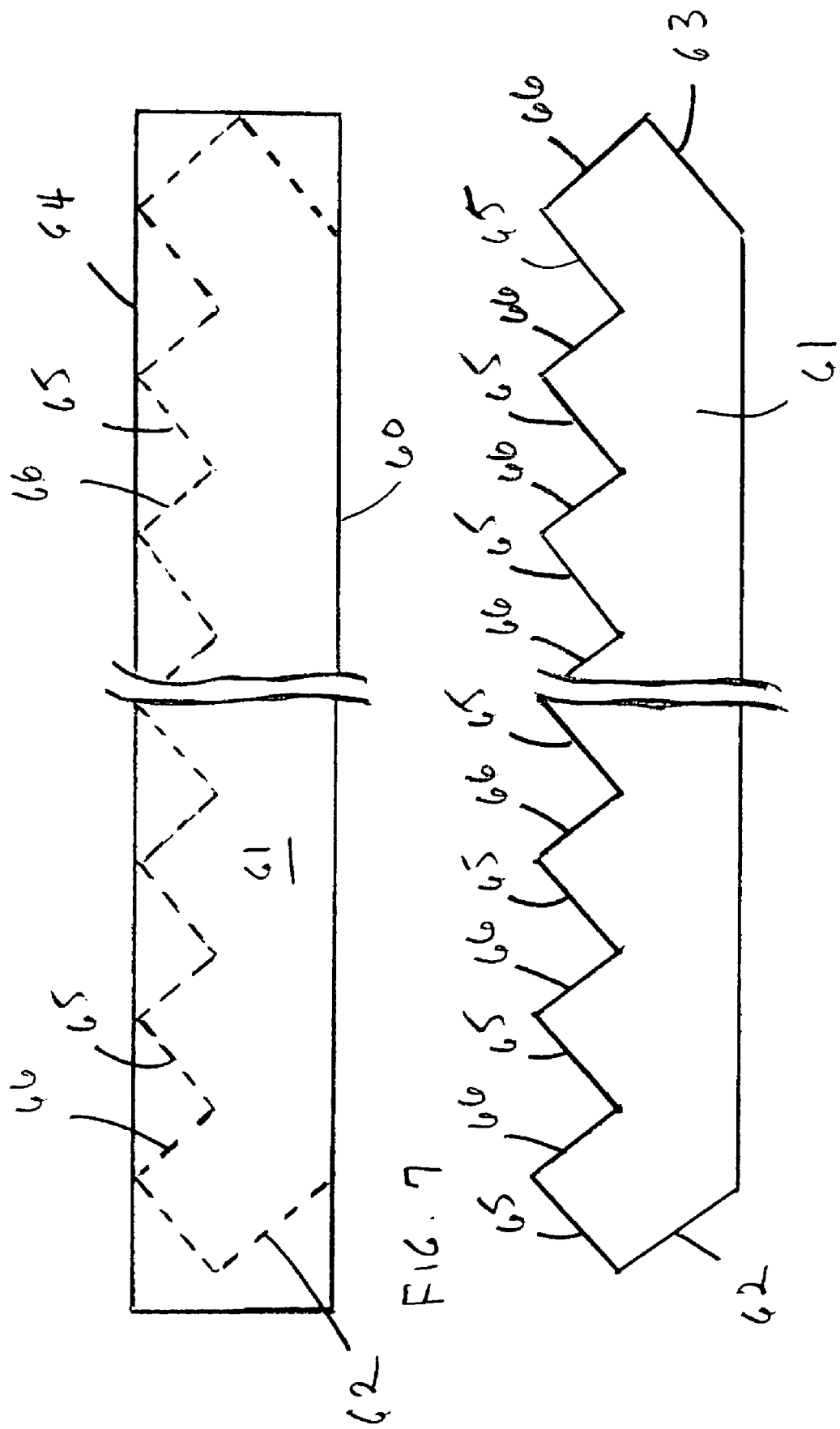

FRAMING SQUARE

BACKGROUND OF THE INVENTION

This invention relates to a combination square and adjustable angle-defining rule for framing roofing and stair construction parts.

One of the objects of the invention is to provide an adjustable square for common rafter cuts and hip & valley cuts. Another object of the invention is to provide an adjustable square for stair stringer rise and run cuts. Still another object of the invention is to provide a plumb for plumb areas difficult to see with regular levels. Another object of the invention is to provide a cutting guide. Still another object of the invention is to provide means for obtaining a 16 inch or 12 inch center layout. Another object of the invention is to provide means for making cuts at angles greater than forty-five degrees. Another object of the invention is to provide a level.

SUMMARY OF THE INVENTION

The present invention meets the above objects by providing a square with longitudinal slots in the angular arms thereof, a rule having a longitudinal slot, and two clamping screws for securing the rule in various angular positions on the arms of the square, so that the scale may be shifted on the square to establish a number of angles, and be maintained at its adjusted position. Spirit levels are provided on each of the square arms and on the rule. The square arms and rule are thick thereby providing saw guides. The square arms are each marked with measuring scales (inches or centimeters), as well as with markers for twelve inch or sixteen inch center layouts. The rule is marked with a plurality of degrees.

These together with other objects of the invention, along with various features of novelty, which characterize the invention, are pointed out with particularity in the claims annexed hereto and forming a part of the disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

FIG. 7 illustrates measurements for rise and run cuts for a stair stringer on a board.
FIG. 8 illustrates the resulting stringer shown in FIG. 7 after the board is cut.

DETAILED DESCRIPTION OF INVENTION

Figure 1:
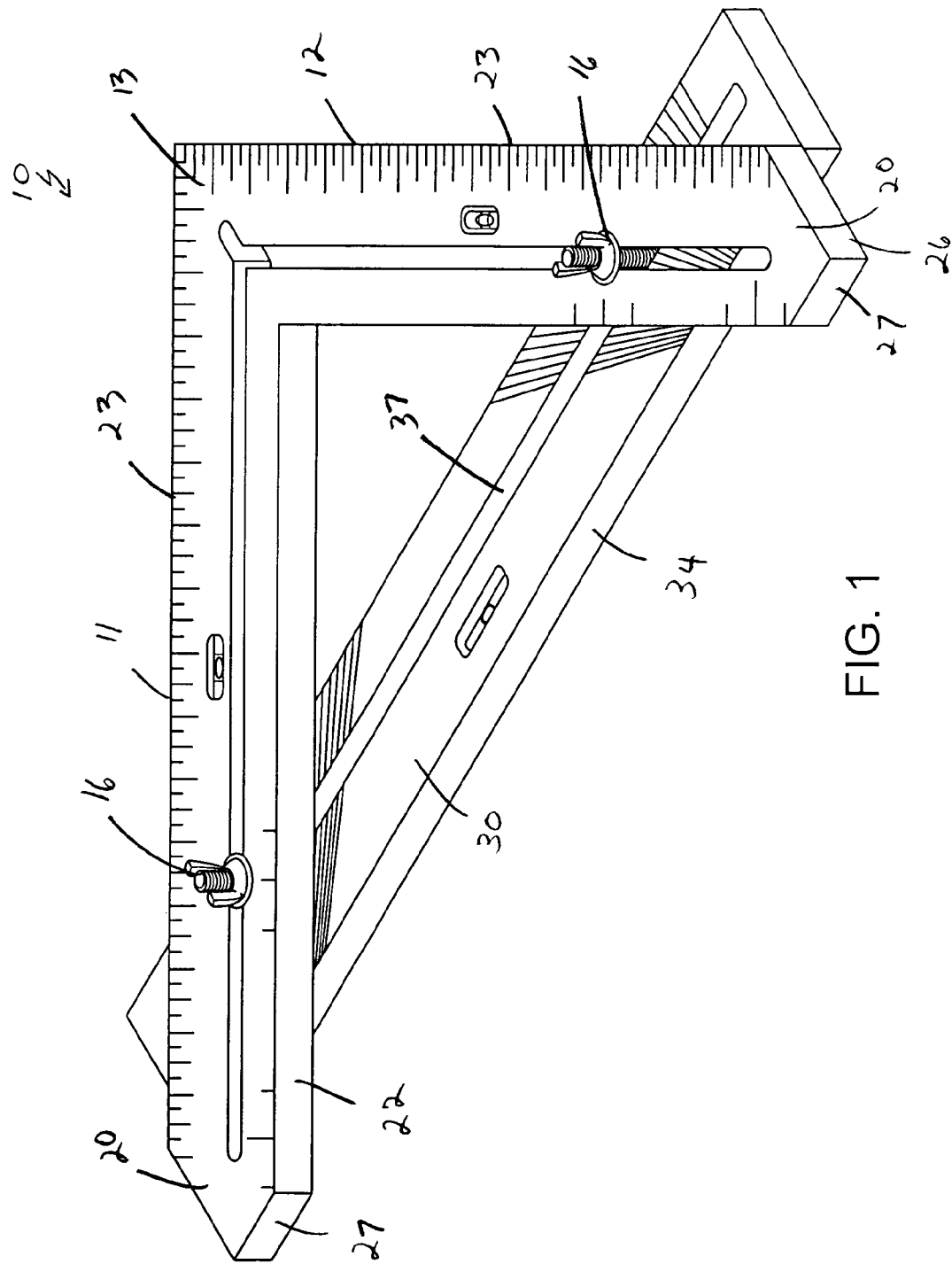
FIG. 1 is a front perspective view of the invention.

Referring to the drawings in detail wherein like elements are indicated by like numerals, there is shown a framing square 10 having a first elongated, generally rectangular, planer arm 11 and a second elongated, generally rectangular, planer arm 12 disposed in right angular relationship thereto. Each arm 11, 12 has a front surface 20, a rear surface 21, an inner side edge 22, an outer side edge 23, a joined end 24 and a free end 25, said arm joined ends 24 forming a framing square junction 13, and said joined end 24 and free end 25 defining a longitudinal axis for each arm 11, 12. The inner side edge 22 of each arm 11, 12 is that edge closest to the nearest edge of the other arm. Each side edge 22, 23 has a thickness, i.e., distance between front surface 20 and rear surface 21, is three quarters of an inch. The free end 25 of each arm 11, 12 is formed in two portions, a first portion 26 extending from the terminus 17 of the outer side edge 23 at a forty-five degree angle to the arm longitudinal axis, and a second portion 27 extending from the terminus 18 inner side edge 22 at a forty-five angle to the arm longitudinal axis and terminating at the first portion 26. The inner side edge terminus 18 is positioned longitudinally past the outer side edge terminus 17. Each arm 11, 12 has an elongated, longitudinal slot 14 extending from a point spaced from the arm joined edge 24 to a point spaced from the arm free end 25, said longitudinal slot having a longitudinal axis coincident with the arm longitudinal axis. The longitudinal slot 14 for each arm 11, 12 joins at the square junction 13, the joined resulting slot 15 extending to a point spaced from a junction of the arm joined end outer side edges 23.

The framing square 10 is further comprised of an elongated, generally rectangular, planer rule 30. The rule 30 has a front surface 31, a rear surface 32, a first side edge 33, an opposite second side edge 34, a left end 35, a right end 36, said left end and right end defining a rule longitudinal axis. The thickness of each side edge, i.e., distance between front surface 31 and rear surface 32, is three quarters of an inch. The rule 30 has an elongated, longitudinal slot 37 formed therein, extending from a point spaced from the rule left end 35 to a point spaced from the rule right end 36. The rule slot 37 has a longitudinal axis coincident with the longitudinal axis of the rule 30.

The square 10 is further comprised of two clamping screws 16, each screw engaging an arm longitudinal slot 14 and protruding through and engaging the rule longitudinal slot 37. Each clamping screw 16 is adapted to being loosened and tightened thereby allowing adjustment of the position of the rule 30 in relationship with the arms 11, 12.

The square 10 is further comprised of a plurality of spirit levels, one spirit level 28 being installed on each arm 11, 12, and another spirit level 38 being installed on the rule 30. The arm spirit levels 28 have longitudinal axes parallel to their respective arm longitudinal axis and are generally positioned between the arm longitudinal slot 14 and the arm outer side edge 23. The rule spirit level 38 has a longitudinal axis parallel to the rule longitudinal axis and is generally positioned between the longitudinal slot 37 and the second side edge 34.

Carpenters must often make many repetitive cuts. For roofing rafters, a carpenter may prepare a number of rafters at one time. To assist the carpenter a number of scales are placed on the framing square. Once the carpenter has set the rule 30 on the square arms 11, 12 along the desired scale, the square may be butted against each successive board and the correct cutting angle will result.

The front surface 20 of each arm 11, 12 is provided with a first scale 40 adjacent to and extending onto the arm outer side edge 23. The first scale 40 is divided into inches and into divisions of four spaces for each inch, representing quarters of an inch. In other embodiments of the invention, the scale may have other distance divisions, i.e., metric, more or less that eight spaces per inch, etc. In this embodiment of the invention, the first scale is sixteen inches long.

The front surface 20 of each arm is also provided with a second scale 41 adjacent the arm inner side edge 22 beginning at the arm free end 25 and extending a designated distance along the inner side edge 22 toward the arm joined end 24. The second scale 41 is used for measuring on center distances of twelve inches and sixteen inches between support elements. A primary indicator line indicates the twelve inch and sixteen inch lines. Supplementary indicator lines are marked three-quarters of an inch on each side of the primary indicator lines.

Figure 2:
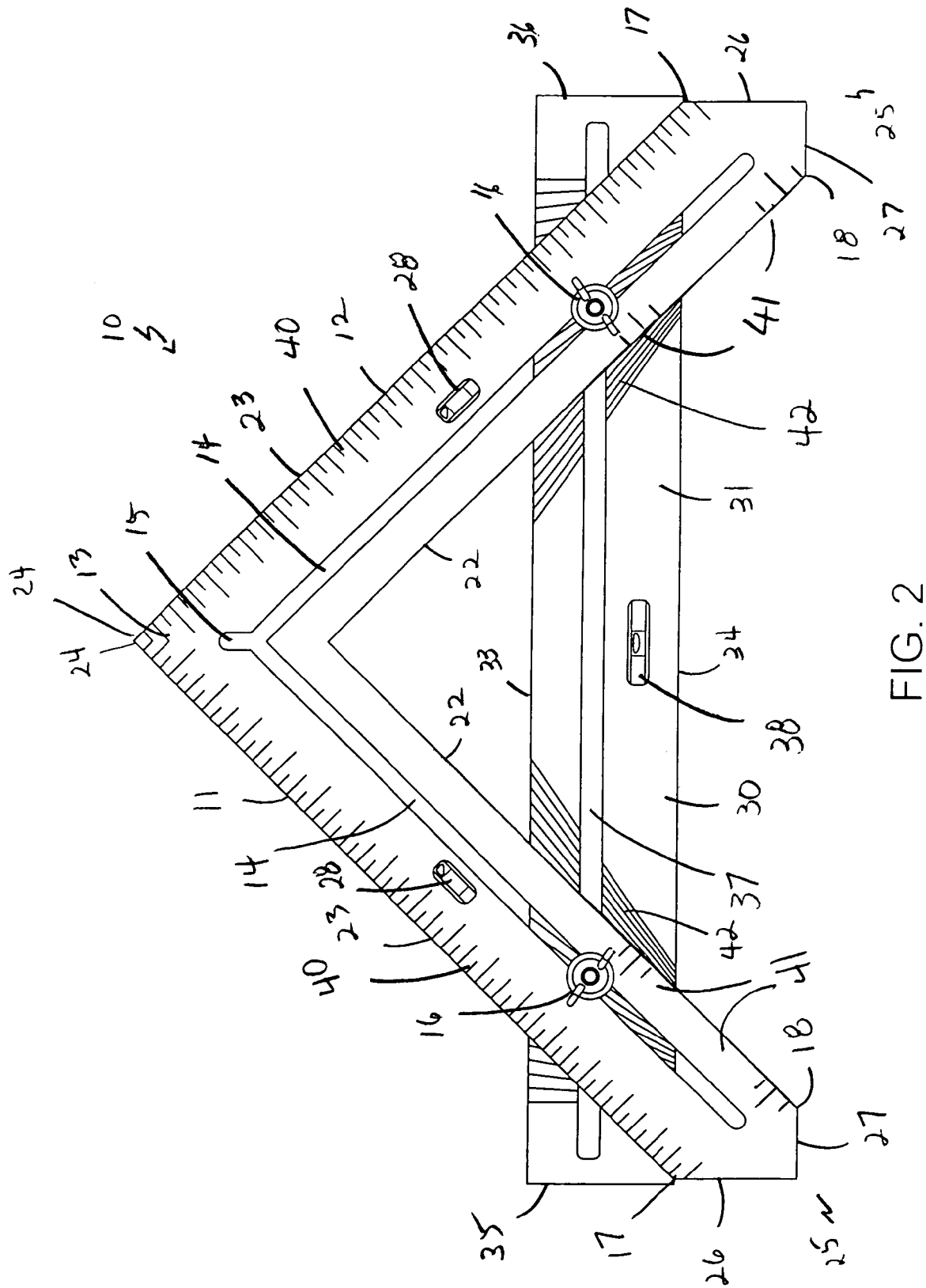
FIG. 2 is a front plan view of the invention.
Figure 3:
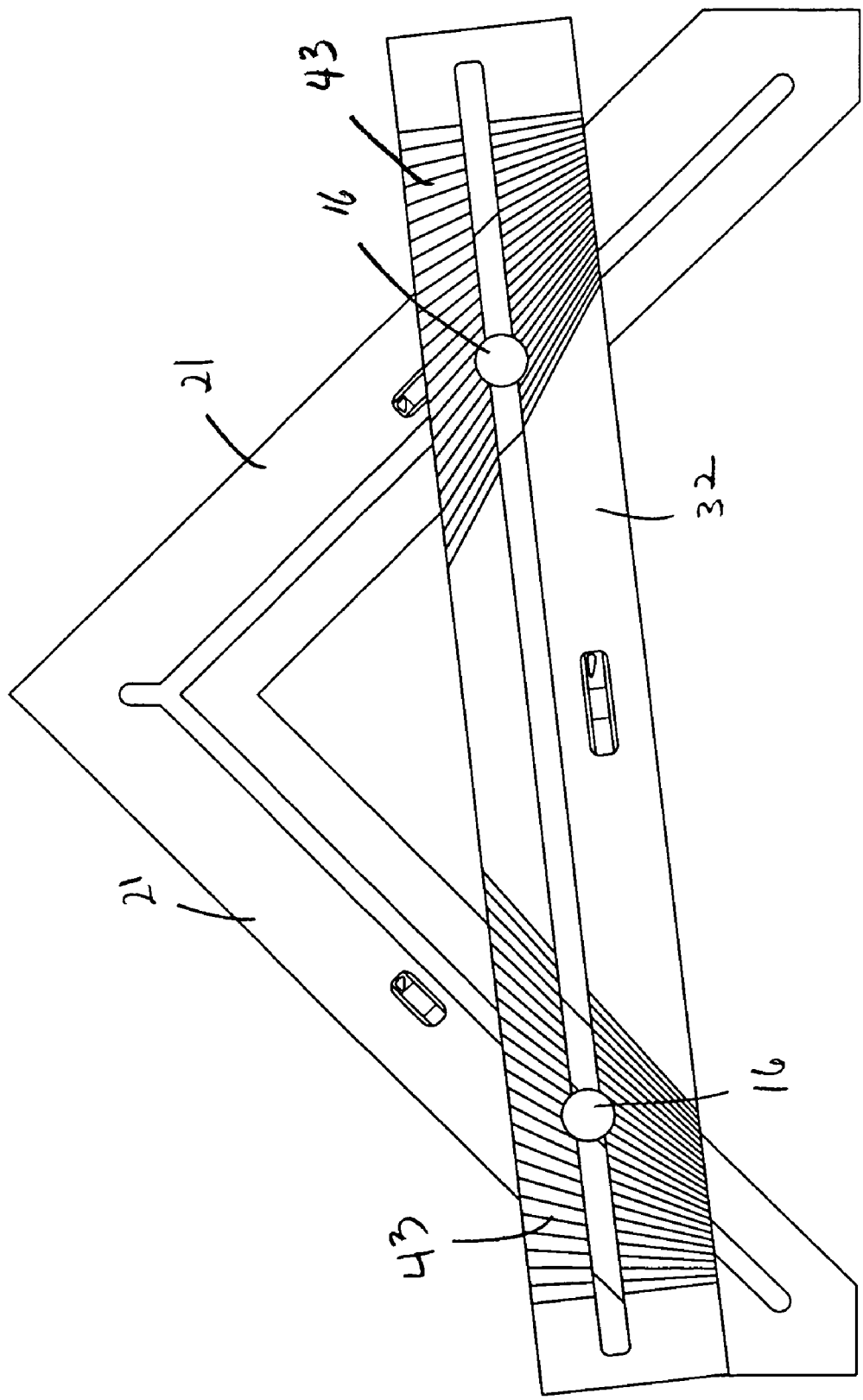
FIG. 3 is a rear plan view of the invention.
Figure 4:
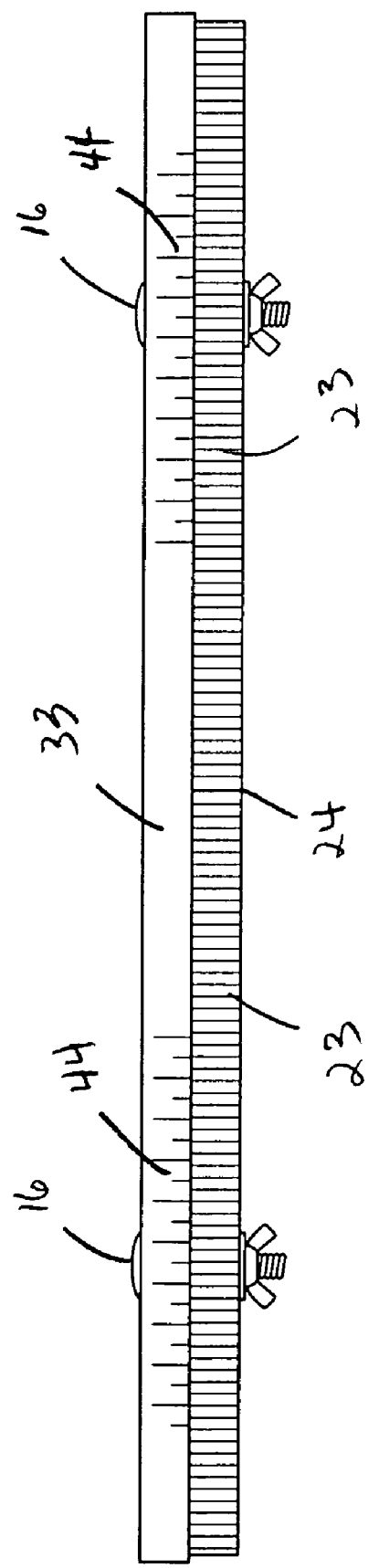
FIG. 4 is a top view of the invention.

The rule front surface 31 is provided with a third scale 42 providing a plurality of angle lines representing common pitch lines for common rafter cuts. The angle lines extend across the rule front surface 31 extending from the rule second side edge 34 to the rule first side 33. See FIG. 2. The rule rear surface 32 is provided with a fourth scale 43 providing a plurality of angle lines representing hip and valley pitch lines for typical hip and valley cuts. See FIG. 3. As is known in the trade, a common pitch line has a different angle than a hip and valley pitch line with the same reference number. This makes the fourth scale especially beneficial for the framing square user. A fifth scale 44 is provided on the rule first side edge 33 providing a plurality of angle lines for degree cuts. The fifth scale 44 provides a conversion scale for common pitch lines to degrees. This permits use of a skill saw instead of a compound saw which is impractical for many applications.

Figure 5:
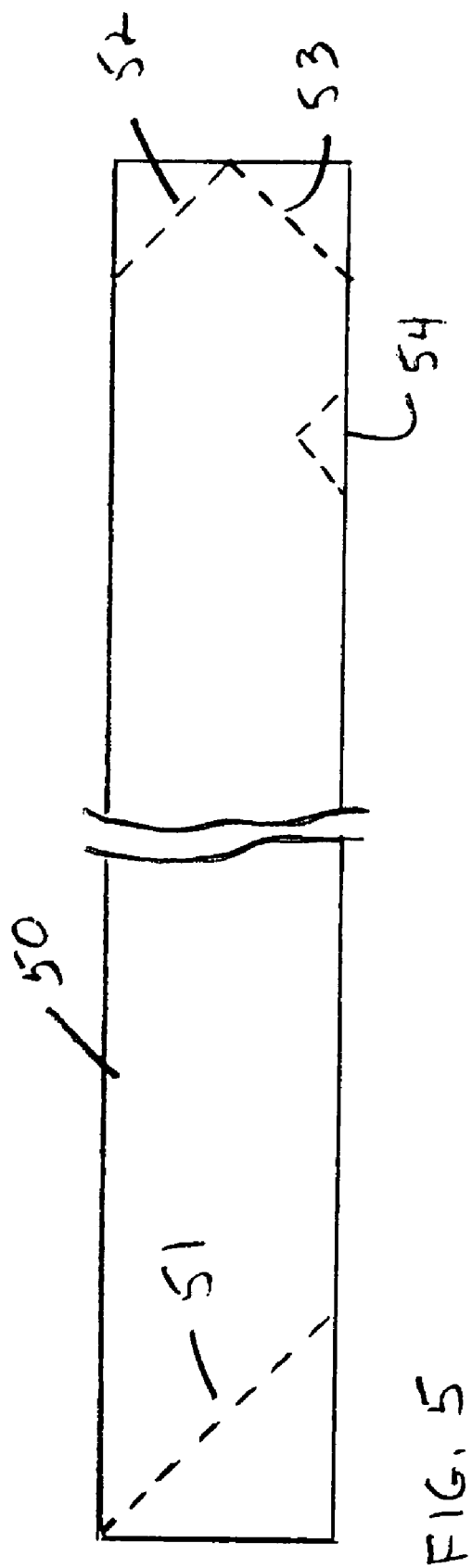
FIG. 5 illustrates measurements for common rafter cuts and hip and valley cuts on a 2×10 rafter.
Figure 6:
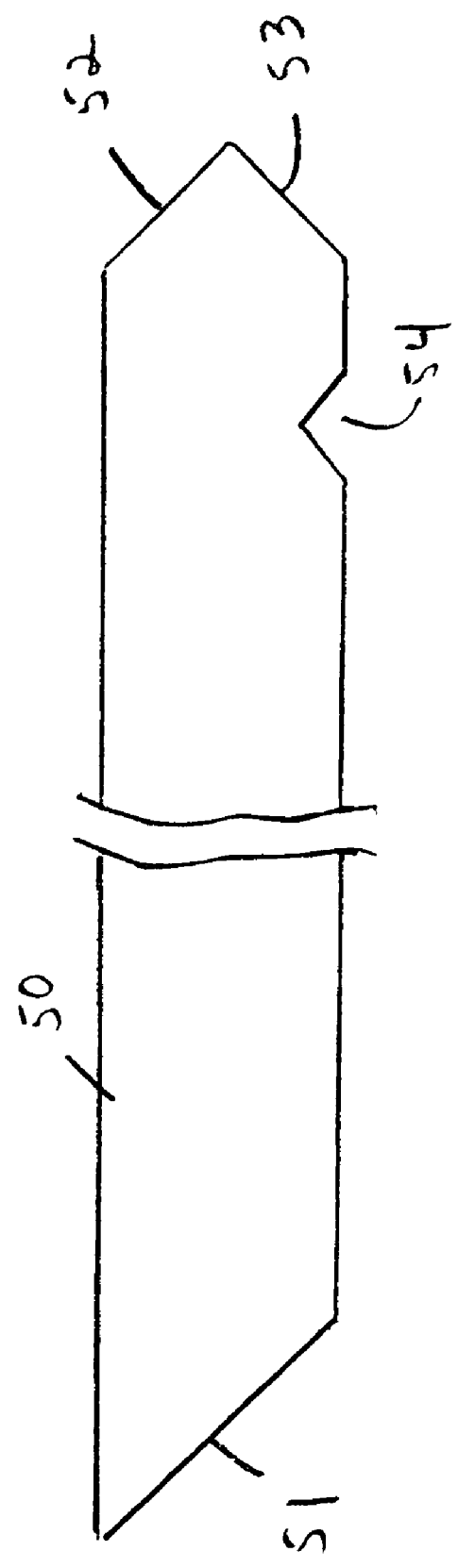
FIG. 6 illustrates the resulting rafter shown in FIG. 5 after the rafter is cut.

Referring more particularly to FIGS. 5 and 6, there is shown a 2×10 rafter 50 marked by the invention framing square 10 in FIG. 5 for a ridge cut 51 at one end, a facia cut 52 at the other end, a soffit 53 adjacent the facia cut and a heel cut 54 along one rafter edge near to said soffit cut. The framing square rule 30 is positioned along the desired common pitch angle indicated in the third scale 42. The framing square 30 is then positioned along the rafter end for marking a ridge cut 51. After the ridge cut 51 is measured, the rule rear surface 32 with the fourth scale 43 is used to mark the hip and valley cuts 52, 53, 54. FIG. 6 shows the resulting rafter after the cuts indicated in FIG. 5 have been made.

Referring more particularly to FIGS. 7 and 8, there is shown a board 60 marked by the invention framing square 10 in FIG. 7 for a stringer 61. The stringer bottom 62, which sits on a subfloor, is marked at one end of the board 60. The stringer top 63, which is nailed to a header, is marked at the other end of the board 60. The framing square rule 30 is positioned so that the rule first side edge 33 is aligned on the arms 11, 12 60 for the desired rise 65 and 66 run measurements. The framing square joined end 24 is then placed on the board slid toward the other board side until the rule first side edge 33 engages one board side edge 64. Moving the framing square along the board side edge 64, the stringer rises 65 and runs 66 are marked. FIG. 8 shows the resulting stringer after the cuts indicated in FIG. 7 have been made.

Figure 9:
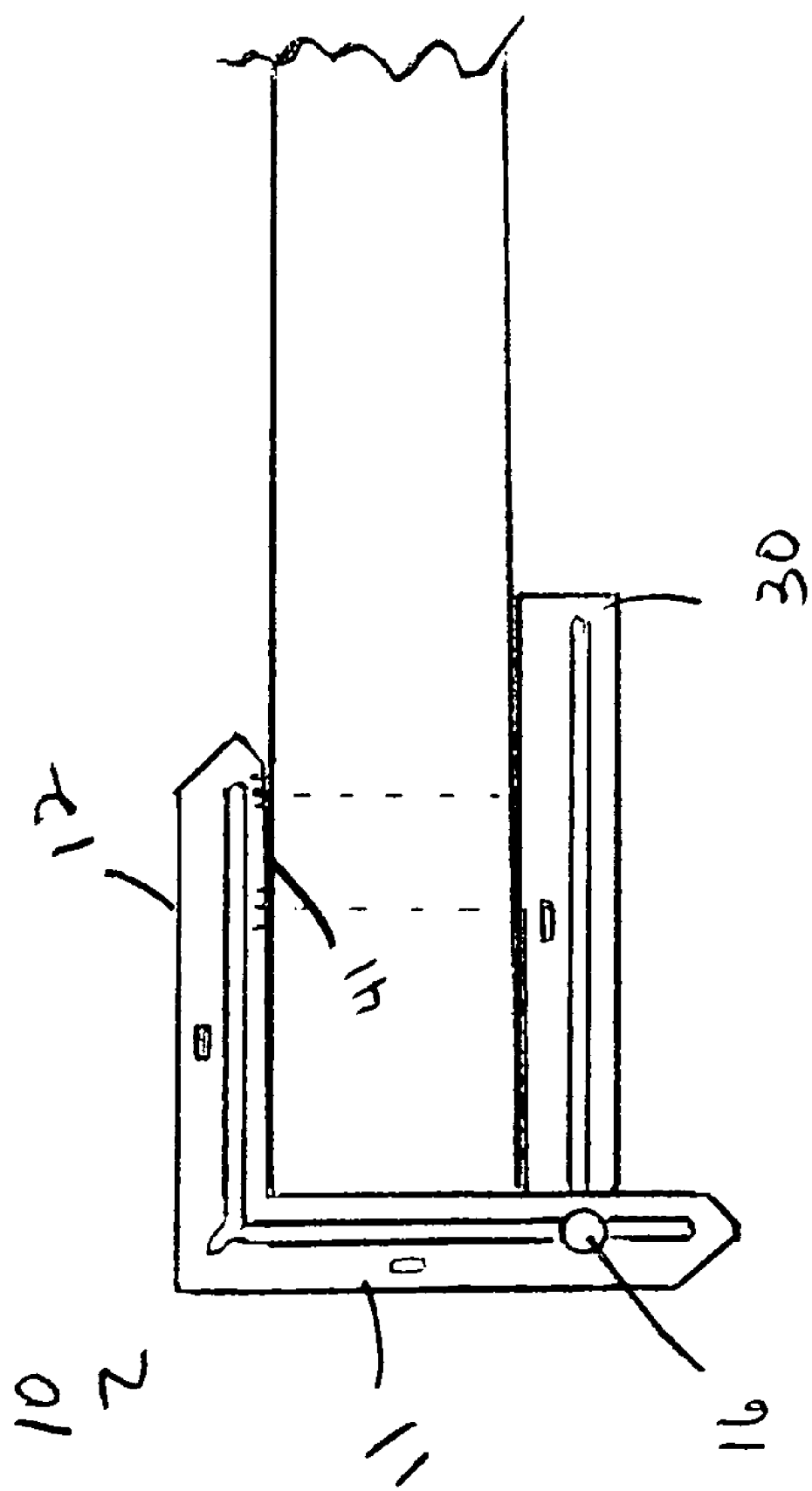
FIG. 9 illustrates the invention framing square used for marking 12 inch or 16 inch center layout.

Referring more particularly to FIG. 9, there is shown the framing square 10 positioned about the end of a board 70 and marked with the second scale 41 to measure on center distances of twelve inches or sixteen inches between support elements. After marking the desired distance the framing square 10 is slid along the board so that the outer side edge 23 of the first arm 11 is aligned with the mark. The board is then marked again at the desired distance and the process repeated until the entire board is marked with on center distances.

Figure 10:
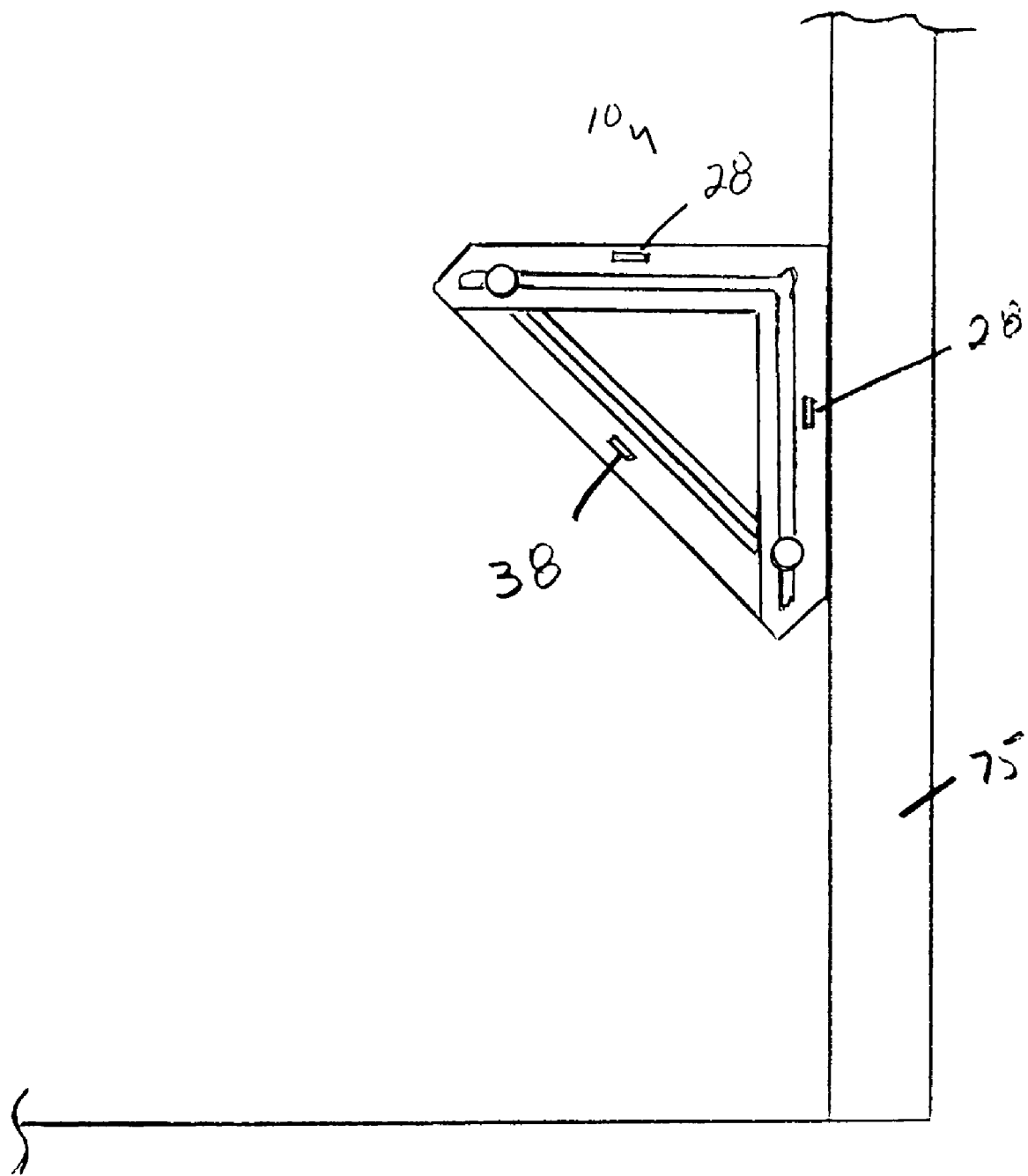
FIG. 10 illustrates the invention framing square used to plumb a post or wall.

Referring more particularly to FIG. 10, the invention framing square 10 is shown used to plumb a post or wall with the framing square spirit levels 28.

It is understood that the above-described embodiment is merely illustrative of the application. Other embodiments may be readily devised by those skilled in the art which will embody the principles of the invention and fall within the spirit and scope thereof.

I claim:

1. An adjustable carpenter's framing square, comprising:

a first elongated, generally rectangular, planar arm;

a second elongated, generally rectangular, planer arm disposed in right angular relationship to said first arm;

wherein each arm has a front surface, a rear surface, an inner side edge, an outer side edge, a joined end and a free end, said arm joined ends forming a framing square junction, said joined end and free and defining longitudinal axis for each arm;

wherein each arm has an elongated, longitudinal slot extending from a point space from the arm joined edge to a point spaced from the arm free end, said longitudinal slot having a longitudinal axis coincident with the arm longitudinal axis;

wherein the free end of each arm is formed in two portions, a first portion extending from a terminus of the outer side edge at a forty-five degree angle to the arm longitudinal axis, and a second portion extending from a terminus of the inner side edge at a forty-five angle to the arm longitudinal axis and terminating at the first portion, the inner side edge terminus being positioned longitudinally past the outer side edge terminus;

an elongated, generally rectangular, planer rule, having a front surface, a rear surface, a first side edge, an opposite second side edge, a left end, a right end, said left end and right end defining a rule longitudinal axis, said rule having an elongated, longitudinal slot formed therein, extending from a point spaced from the rule left end to a point spaced from the right end, said rule slot having a longitudinal axis coincident with the longitudinal axis of the rule;

two clamping screws, each screw engaging an arm longitudinal slot and protruding through and engaging the rule longitudinal slot, each clamping screw adapted to being loosened and tightened thereby allowing adjustment of the position of the rule in relationship to the arms;

a plurality of spirit levels, one spirit level being installed on each arm and another spirit level being installed on the rule, wherein the arm spirit levels each have longitudinal axes parallel to their respective arm longitudinal axis and are generally positioned between the arm longitudinal slot and the arm outer side edge, and the rule spirit level has a longitudinal axis parallel to the rule longitudinal axis and is generally positioned between the longitudinal slot and the second side edge;

a plurality of scales comprising:

a first scale on the front surface of each arm, adjacent to and extending onto the arm outer side edge, said first scale presenting a linear distance scale;

a second scale on the front surface of each arm, adjacent the arm inner side edge beginning at the arm free end and extending a designated distance along the inner side edge toward the arm joined end, said second scale presenting on center distances of twelve inches and sixteen inches between support elements;

a third scale on the rule front surface presenting a plurality of angle lines representing common pitch lines for common rafter cuts;

a fourth scale on the rule rear surface presenting a plurality of an lines representing hip and valley pitch lines;

a fifth scale on the rule first side edge presenting a plurality of angle lines for degree cuts providing a conversion scale for common pitch lines to degrees.

2. An adjustable carpenter's framing square as recited in claim 1, wherein:

the longitudinal slot for each arm joins at the square junction, a joined resulting slot extending to a point spaced from a junction of the arm joined end outer side edges.

3. An adjustable carpenter's framing square as recited in claim 2, wherein:

the first scale is divided into inches and is sixteen inches long;

the second scale has a primary scale line indicating a twelve inch point and a sixteen inch point;

the third scale angle lines extend across the rule front surface extending from the rule second side edge to the rule first side edge;

the fourth scale angle lines extend across the rule rear surface extending from the rule second side edge to the rule first side edge.

\* \* \* \* \*